US012691302B2

(12) United States Patent
Kaminski

(10) Patent No.: US 12,691,302 B2
(45) Date of Patent: Jul. 28, 2026

(54) OPTICAL SURFACE TRACKING CAMERA PLACEMENT FOR RADIOTHERAPY

(71) Applicant: Elekta Limited, Crawley (GB)

(72) Inventor: Kamil Kaminski, Crawley (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 18/495,050

(22) Filed: Oct. 26, 2023

(65) Prior Publication Data

US 2024/0139545 A1 May 2, 2024

(30) Foreign Application Priority Data

Oct. 26, 2022 (GB) ...................................... 2215817

(51) Int. Cl.
*A61N 5/10* (2006.01)
*G01S 17/894* (2020.01)

(52) U.S. Cl.
CPC ......... *A61N 5/1049* (2013.01); *A61N 5/1081* (2013.01); *G01S 17/894* (2020.01); *A61N 2005/1059* (2013.01)

(58) Field of Classification Search
CPC ............................ A61N 5/1049; A61N 5/1081
See application file for complete search history.

(56) References Cited

U.S. PATENT DOCUMENTS 11,369,806 B2    6/2022   Laurence, Jr. et al.
2007/0003010 A1  1/2007   Guertin et al.

2007/0014391 A1   1/2007  Mostafavi et al.
2016/0035108 A1   2/2016  Yu et al.
2016/0249984 A1*  9/2016  Janssen ................... A61B 34/25
                                                600/427
2018/0014745 A1*  1/2018  Senegas ............... A61B 5/1128
2019/0321657 A1  10/2019  Hale
2020/0097755 A1   3/2020  Li et al.
2021/0146158 A1   5/2021  Wirtz et al.
2021/0263137 A1   8/2021  Dehlinger et al.
2021/0341620 A1* 11/2021  Raz ........................ G01S 17/894

(Continued)

FOREIGN PATENT DOCUMENTS

EP        3783379 A1    2/2021
EP        4124875       2/2023

(Continued)

OTHER PUBLICATIONS

"United Kingdom Application Serial No. 2215817.4, Examination Report dated Apr. 17, 2023", (Apr. 17, 2023), 5 pgs.

(Continued)

*Primary Examiner* — Thanh Luu
(74) *Attorney, Agent, or Firm* — Schwegman Lundberg & Woessner, P.A.

(57) ABSTRACT

A radiotherapy device and a method for imaging a subject using a radiotherapy device are provided. The radiotherapy device comprises a rotatable gantry, a support surface and a plurality of cameras. The rotatable gantry comprises a front, a rear and a bore. The support surface is moveable into the bore from a side of the radiotherapy device corresponding to the front of the rotatable gantry. The plurality of cameras are for monitoring a subject that is located on the support surface, the plurality of cameras including a rear camera disposed adjacent to the rear of the rotatable gantry.

19 Claims, 6 Drawing Sheets

(56)            References Cited

U.S. PATENT DOCUMENTS

2022/0203130 A1 *   6/2022  Vojan ..................... G16H 50/20
2024/0177627 A1 *   5/2024  Nakamura ................ G06T 7/70

FOREIGN PATENT DOCUMENTS

WO      WO-2021032606 A1 *   2/2021    ........... A61B 5/0033
WO           2022036442        2/2022

OTHER PUBLICATIONS

"European Application Serial No. 23204746.4, European Search Report dated Feb. 29, 2024", (Feb. 29, 2024), 9 pgs.
"European Application No. 23 204 746.4, Office Action dated May 13, 2026", May 13, 2026, 5 pgs.

* cited by examiner

400

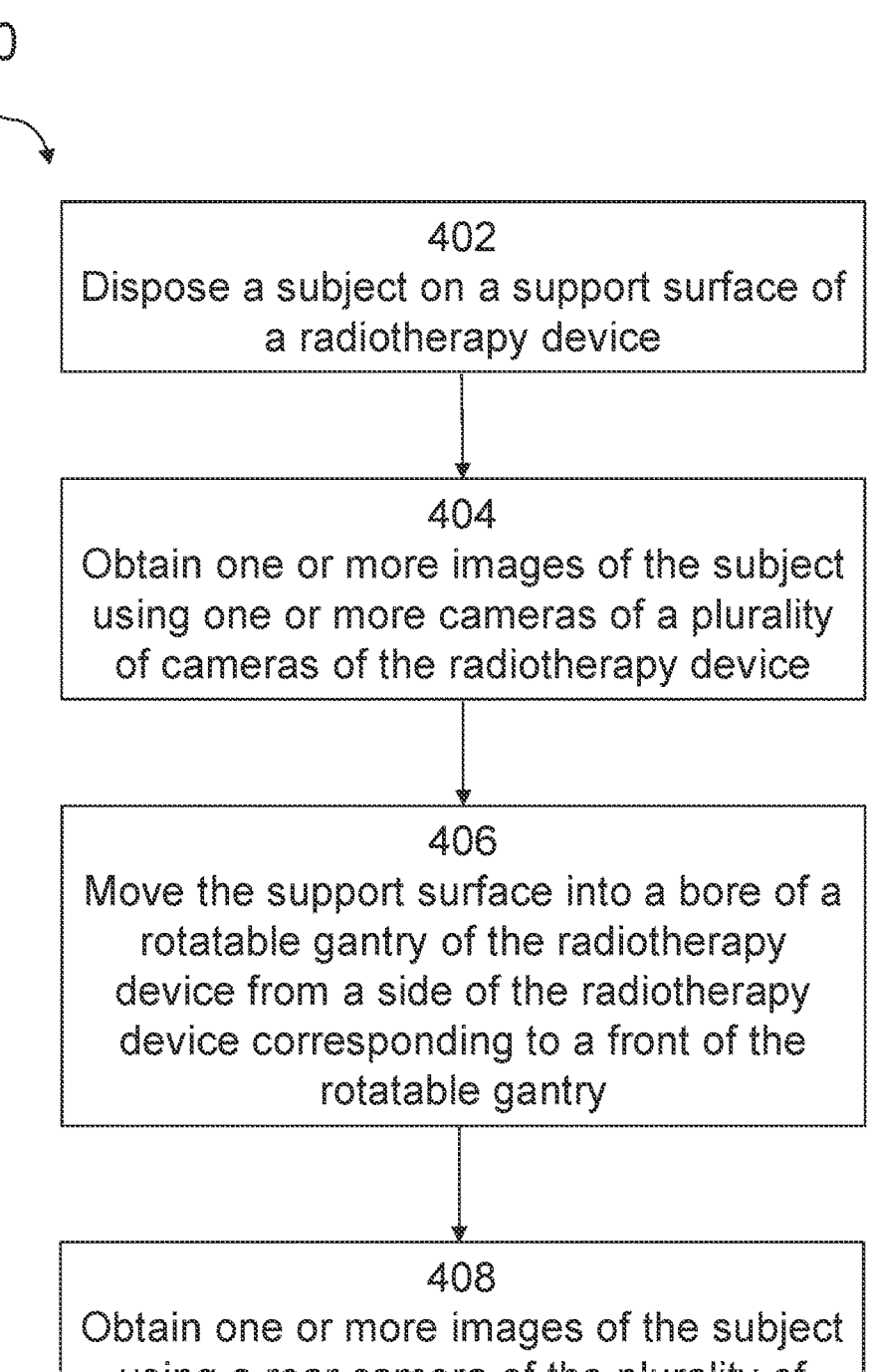

402
Dispose a subject on a support surface of a radiotherapy device

404
Obtain one or more images of the subject using one or more cameras of a plurality of cameras of the radiotherapy device 406
Move the support surface into a bore of a rotatable gantry of the radiotherapy device from a side of the radiotherapy device corresponding to a front of the rotatable gantry 408
Obtain one or more images of the subject using a rear camera of the plurality of cameras, the rear camera being disposed adjacent to a rear of the rotatable gantry

Fig. 4

OPTICAL SURFACE TRACKING CAMERA PLACEMENT FOR RADIOTHERAPY

CLAIM FOR PRIORITY

This application claims the benefit of priority of British Application No. 2215817.4, filed Oct. 26, 2022, which is hereby incorporated by reference in its entirety.

TECHNICAL FIELD

This disclosure relates to optical surface tracking for radiotherapy, and in particular to placement of cameras for optical surface tracking.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device may comprise a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc.

In radiotherapy treatment, it is desirable to deliver a prescribed dose of radiation to a target region of a subject and to limit irradiation of other parts of the subject, (e.g., of healthy tissue). In view of this, a radiotherapy device may comprise one or more imaging devices for capturing images of the patient before and/or during a radiotherapy treatment, which can be used to make adjustments to machine parameters or patient location. Image-guided radiation therapy (IGRT) can improve the accuracy of radiotherapy treatments through confirming that the internal anatomy of the patient is in the expected locations. Surface-guided radiation therapy (SGRT) can improve the accuracy of radiotherapy treatments through confirming that the surface of the patient is in the expected locations.

SUMMARY

Before a radiotherapy treatment is started, the patient may be positioned in a suitable position for the radiotherapy treatment. This is referred to herein as the setup phase. The setup phase may involve positioning particular parts of the patient in particular locations and/or at particular angles, in some cases with use of one or more accessories for assisting the patient in taking up and maintaining a desired posture. Subsequently to the setup phase, the radiotherapy treatment may be delivered to the patient. This is referred to herein as the treatment phase. The treatment phase involves delivering a radiotherapy beam to irradiate and thereby treat one or more target regions in the patient.

SGRT can be used in the setup phase to verify that the patient is in the desired location and posture before the radiotherapy treatment starts, and/or can be used in the treatment phase to verify that the patient remains in the desired location and posture during the radiotherapy treatment. For the setup phase and/or the treatment phase, visual tracking of the surface of the patient disposed on a patient couch of the radiotherapy device may be performed. The visual tracking may be performed using any suitable imaging modality, including those using 2D cameras/technologies and/or 3D cameras/technologies. The visual tracking may be performed, for example, using one or more visible light cameras (e.g. one or more 2D RGB cameras), one or more structured light cameras, one or more LIDAR cameras, one or more stereo vision cameras and/or one or more time-of-flight cameras. The visual tracking may monitor the respective locations of a plurality of points on the surface of the subject and determine displacements of each of the points from their previous positions. The visual tracking may monitor the surface of the patient and its displacement relative to a pre-treatment scan. The visual tracking may be used to infer the locations and/or motions of the internal anatomy of the patient.

A radiotherapy device may include a ring-shaped rotatable gantry comprising a central bore within which the patient is positioned during treatment. The patient couch may be moveable, e.g. translatable, between a location outside the bore and a location inside the bore. In the setup phase, the patient may be disposed on the patient couch with the patient couch outside the bore. The patient couch with the patient disposed thereon may then be moved into the bore such that, in the treatment phase, the patient may be disposed on the patient couch with the patient couch inside the bore. The geometry of bore-based radiotherapy devices can pose a challenge for SGRT systems since it can be difficult to observe the patient in the treatment phase. For example, while cameras in the room containing the radiotherapy device may have lines of sight to the patient in the setup phase, in the treatment phase one or more of these lines of sight may be partially or completely blocked by the bore. This may prevent or limit the capability to accurately monitor the surface of the patient.

It would be advantageous to provide more accurate imaging of the surface of a patient and thereby to provide more accurate surface-guided radiotherapy. It would also be advantageous to provide more optimised imaging of the surface of a patient in both setup and treatment phases. It would also be advantageous to increase the volume imaged in and around the radiotherapy device. It would also be advantageous to maximise patient visibility while taking into account the geometrical and space limitations associated with other components of the radiotherapy device.

According to an aspect of the present disclosure, there is provided a radiotherapy device comprising: a rotatable gantry comprising a front, a rear and a bore; a support surface moveable into the bore from a side of the radiotherapy device corresponding to the front of the rotatable gantry. The radiotherapy device may further comprise a plurality of cameras for monitoring a subject that is located on the support surface, the plurality of cameras including a rear camera disposed adjacent to the rear of the rotatable gantry.

According to a further aspect, there is provided a method for imaging a subject using a radiotherapy device comprising a rotatable gantry, a support surface, and a plurality of cameras, the method comprising: moving the support surface with the subject disposed thereon into a bore of the rotatable gantry from a side of the radiotherapy device corresponding to a front of the rotatable gantry. The method may further comprise obtaining one or more images of the subject using a rear camera of the plurality of cameras, the rear camera being disposed adjacent to a rear of the rotatable gantry.

BRIEF DESCRIPTION OF THE DRAWINGS

Specific embodiments are now described, by way of example only, with reference to the drawings, in which:

FIG. 4 depicts a method of imaging a subject according to the present disclosure;

DETAILED DESCRIPTION

The present disclosure provides a radiotherapy device comprising a rotatable gantry which includes a front, a rear and a bore. The radiotherapy device also comprises a support surface which is moveable into the bore. The support surface is moveable into the bore from a side of the radiotherapy device corresponding to the front of the rotatable gantry. The radiotherapy device also comprises a plurality of cameras for monitoring a subject located on the support surface. One of the plurality of cameras is disposed adjacent to the rear of the rotatable gantry. This camera may be referred to as a rear camera of the plurality of cameras.

The location of the rear camera enables it to provide useful data on the locations of surfaces of the subject when disposed inside the bore. In particular, this positioning of the rear camera means its field of view is not obscured by the structure of the rotatable gantry defining the bore or other components of the radiotherapy device. The location of the rear camera may be particularly useful for viewing parts of the subject disposed towards the rear of the bore, for example the head and upper body of the subject, during the treatment phase. The data from this rear camera may be cross-referenced, correlated or combined with the data from one or more of the other cameras of the plurality of cameras in order to increase the accuracy of the surface measurements obtained for the subject. The viewing angle of the rear camera to the parts of the subject located towards the rear of the bore may be closer to perpendicular than would be provided by views from cameras at the front of the bore, which may advantageously enable spatial averaging over a plurality of spatial measurements so as to increase the accuracy of the acquired data. The location of the rear camera to the rear of the bore may advantageously provide this improvement in the views acquired and improvement in the accuracy of the acquired data while avoiding taking up space within the bore, which may have tight space constraints and may need to accommodate a range of sizes and shapes of patients.

Figure 1:
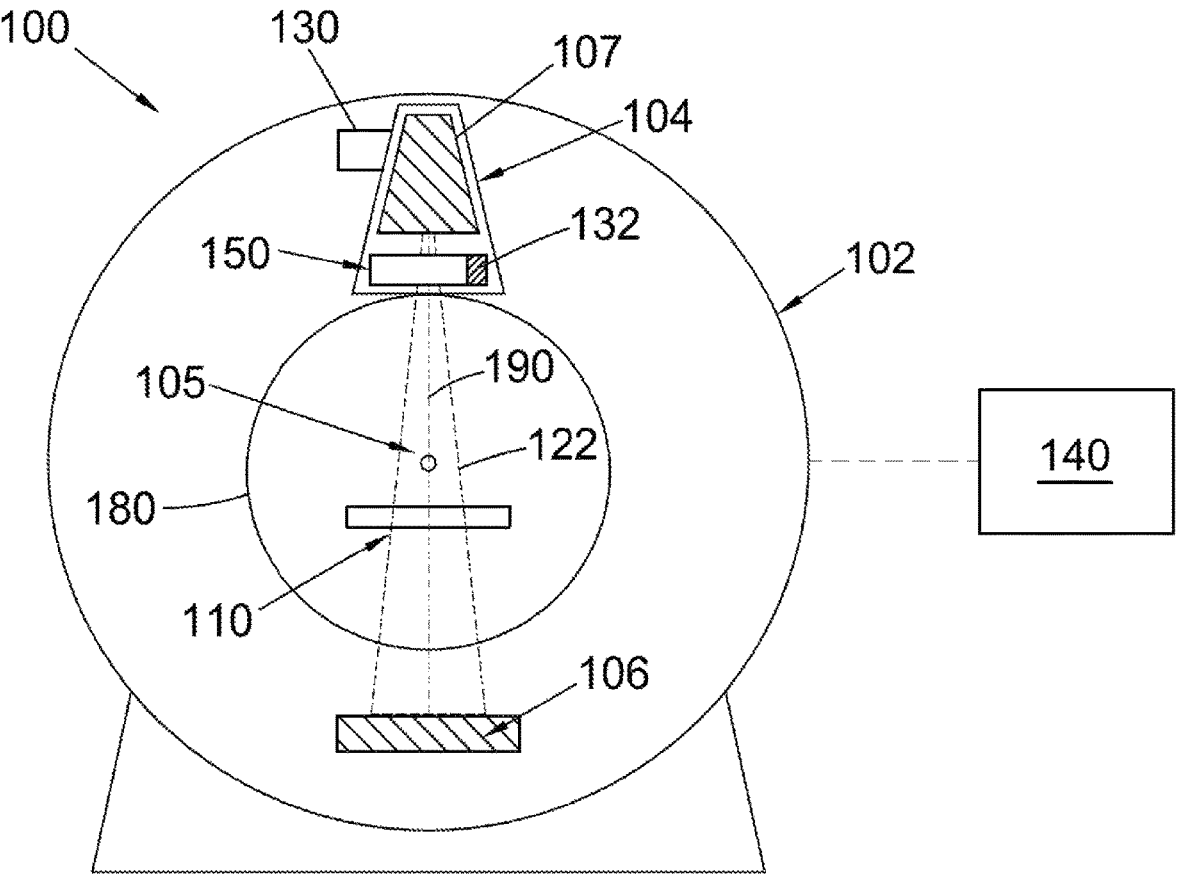
FIG. 1 depicts an example of a radiotherapy device or apparatus according to the present disclosure.

FIG. 1 depicts an example of a radiotherapy device 100 according to the present disclosure. The Figure shows a cross-section through the radiotherapy device 100 comprising a radiation head 104 and a beam receiving apparatus 106, both of which are attached to a rotatable gantry 102. The radiation head 104 includes a radiation source 107 which emits a beam of radiation 122. The radiation head 104 also includes a beam shaping apparatus 150 which controls the size and shape of the radiation field associated with the beam.

The beam receiving apparatus 106 is configured to receive radiation emitted from the radiation head 104, for the purpose of absorbing and/or measuring the beam of radiation. In the view shown in FIG. 1, the radiation head 104 and the beam receiving apparatus 106 are positioned diametrically opposed to one another.

The gantry 102 is rotatable, and supports the radiation head 104 and the beam receiving apparatus 106 such that they are rotatable around an axis of rotation 105, which may coincide with the superior-inferior axis of the patient when positioned in the radiotherapy device 100 for treatment. As shown in FIG. 1, the gantry provides rotation of the radiation head 104 and the beam receiving apparatus 106 in a plane which is perpendicular to the superior-inferior axis.

FIG. 1 also shows a support surface 110 on which a subject (or patient) is supported during radiotherapy treatment. The radiation head 104 is configured to rotate around the axis of rotation 105 such that the radiation head 104 directs radiation towards the subject from various angles around the subject in order to spread out the radiation dose received by healthy tissue to a larger region of healthy tissue while building up a prescribed dose of radiation at a target region.

The radiotherapy device 100 is configured to deliver a radiation beam towards a radiation isocentre which is substantially located on the axis of rotation 105 at the centre of the gantry 102 regardless of the angle at which the radiation head 104 is placed.

The gantry 102 may be ring-shaped. In other words, the gantry 102 may be a ring-gantry. A patient or subject is positioned on the support surface 110 during radiotherapy treatment. The radiotherapy device 100 may comprise a bore defined by the ring-shaped gantry 102, within which the subject is positioned during treatment. The support surface 110 may be moveable in one or more translational degrees of freedom and one or more rotational degrees of freedom. The support surface 110 may be used to move the subject from a setup position outside the bore 180 to a treatment position inside the bore 180, i.e. encircled by the gantry 102. This may be achieved by translating the support surface 110 with the subject thereon in a direction parallel to the axis of rotation 105 of the gantry 102. The movement of the support surface 110 may be effected and controlled by one or more actuators and/or motors.

As shown in FIG. 1, the radiation head 104 emits the radiation beam 122 along a beam axis 190 (or radiation axis or beam path), where the beam axis 190 is used to define the direction in which the radiation is emitted by the radiation head 104. The radiation beam 122 is incident on the beam receiving apparatus 106 which can include at least one of a beam stopper and a radiation detector. The beam receiving apparatus 106 is attached to the gantry 102 on a diametrically opposite side to the radiation head 104 in order to attenuate and/or detect a beam of radiation after the beam has passed through the subject. The radiation beam axis 190 may be defined as, for example, a centre of the radiation beam 122 or a point of maximum intensity. The beam receiving apparatus 106 may comprise an imaging panel. The imaging panel may be configured to produce signals indicative of the intensity of radiation incident on the imaging panel. In use, these signals are indicative of the intensity of radiation which has passed through the subject. These signals may be processed to form an image of the subject.

The beam shaping apparatus 150 delimits the spread of the radiation beam 122. The beam shaping apparatus 150 is configured to adjust the shape and/or size of a field of radiation produced by the radiation source. The beam shaping apparatus 150 does this by defining an aperture (also referred to as a window) of variable shape to collimate the radiation beam 122 to a chosen cross-sectional shape. In this example, the beam shaping apparatus 150 is provided by a combination of a diaphragm and a multi-leaf collimator (MLC).

The radiotherapy device 100 may be configured to deliver both coplanar and non-coplanar (also referred to as tilted) modes of radiotherapy treatment. In coplanar treatment, radiation is emitted in a plane which is perpendicular to the axis of rotation of the radiation head 104. In non-coplanar treatment, radiation is emitted at an angle which is not perpendicular to the axis of rotation. In order to deliver coplanar and non-coplanar treatment, the radiation head 104 can move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

The radiation head 104 may be connected to a head actuator 130 which is configured to actuate the radiation head 104 between a coplanar configuration and one or more non-coplanar configurations. In some implementations, the head actuator includes a curved rail along which the radiation head 104 is moved to adjust the position and angle of the radiation head 104. The controller 140 controls the configuration of the radiation head 104 via the head actuator 130.

In the coplanar configuration, the radiation head 104 is positioned to rotate about the axis of rotation 105 in a first plane. In the non-coplanar configuration, the radiation head 104 may be tilted with respect to the first plane such that a field of radiation produced by the radiation head 104 is directed at an oblique angle relative to the first plane. In the non-coplanar configuration, the radiation head 104 may be positioned to rotate in a respective second plane parallel to and displaced from the first plane. The radiation beam 122 may be emitted at an oblique angle with respect to the second plane, and therefore as the radiation head 104 rotates the radiation beam 122 may sweep out a cone shape.

The beam receiving apparatus 106 may remain in the same place relative to the rotatable gantry when the radiotherapy device is in both the coplanar and non-coplanar modes. Therefore, the beam receiving apparatus 106 may be configured to rotate about the axis of rotation 105 in the same plane in both coplanar and non-coplanar modes. This may be the same plane as the plane in which the radiation head 114 rotates. The beam shaping apparatus 150 may be configured to reduce the spread of the field of radiation in the non-coplanar configuration in comparison to the coplanar configuration.

The radiotherapy device 100 includes a controller 140 which is programmed to control one or more of the radiation source 107, the beam receiving apparatus 106, the rotatable gantry 102 and/or other components of the radiotherapy device 100. The controller 140 may perform functions or operations such as treatment planning, treatment execution, image acquisition, image processing, motion tracking, motion management, and/or other tasks involved in a radiotherapy process.

Controller 140 is programmed to control features of radiotherapy device 100 according to a radiotherapy treatment plan for irradiating a target tissue of a patient. The treatment plan includes information about a particular dose to be applied to a target tissue, as well as other parameters such as beam angles, dose-histogram-volume information, the number of radiation beams to be used during therapy, the dose per beam, and the like. Controller 140 is programmed to control various components of radiotherapy device 100, such as gantry 102, radiation head 104, beam receiving apparatus 106, and support surface 110, according to the treatment plan. The controller 140 may be communicatively coupled to one or more of these components, or other components, of the radiotherapy device 100.

Hardware components of controller 140 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

The controller 140 may be formed by several discrete processors; for example, the controller 140 may comprise a processor for each of the various individual components of the radiotherapy device as described herein. The controller 140 may be communicatively coupled to a memory, e.g. a computer readable medium. The controller 140 may be communicatively coupled to one, multiple or all of the various individual components of the radiotherapy device 100 as described herein. As used herein, the controller 140 may also be referred to as a control device. The controller 140 may be communicatively coupled to and may be configured to send control signals to multiple different components of the radiotherapy device 100, for example those described above and elsewhere herein. The controller may be configured to send control signals to one or more components of the radiotherapy device 100 in order to effect changes in radiotherapy treatment and/or imaging of the subject. The controller 140 may also collect data indicative of the performance and actions of various components of the radiotherapy device 100.

The beam shaping apparatus 150 may include a shaping actuator 132. The shaping actuator is configured to control the position of one or more elements in the beam shaping apparatus 150 in order to shape the radiation beam 122. In some implementations, the beam shaping apparatus 150 includes an MLC and a diaphragm, and the shaping actuator 132 includes means for actuating leaves of the MLC and means for actuating blocks of the diaphragm. The controller 140 controls the beam shaping apparatus 150 via the shaping actuator 132.

The radiotherapy device 100 may comprise one or more sources of kV or MV radiation and one or more detectors configured to detect the kV or MV radiation to generate a plurality of images of a subject between the source and the detector. In particular, the radiotherapy device 100 comprises the radiation head 104 configured to emit or direct therapeutic radiation, e.g. MV energy radiation, towards the subject as radiation beam 122. The radiation head 104 may be described as an MV beam source. The radiation head 104 may emit radiation suitable for treating the subject and may emit radiation suitable for generating one or more images of the subject.

The radiotherapy device 100 may comprise a source of radiofrequency waves, an electron source and a waveguide in which the electrons may be accelerated towards a heavy metal, e.g. tungsten, target to produce high energy photons.

The source of radiofrequency waves may be coupled to the waveguide via a circulator, and may be configured to pulse radiofrequency waves into the waveguide. Radiofrequency waves may pass from the source of radiofrequency waves through an RF input window and into an RF input connecting pipe or tube. The source of electrons, such as an electron gun, may also be coupled to the waveguide and may be configured to inject electrons into the waveguide. In the electron gun, electrons may be thermionically emitted from a cathode filament as the filament is heated. The temperature of the filament controls the number of electrons injected. The injection of electrons into the waveguide may be synchronised with the pumping of the radiofrequency waves into the waveguide. The design and operation of the source of radiofrequency waves, electron source and the waveguide may be such that the radiofrequency waves accelerate the electrons to very high energies as the electrons propagate through the waveguide.

The design of the waveguide depends on whether the linac accelerates the electrons using a standing wave or travelling wave, though the waveguide may comprise a series of cells or cavities, each cavity connected by a hole or 'iris' through which the electron beam may pass. The cavities are coupled in order that a suitable electric field pattern is produced which accelerates electrons propagating through the waveguide. As the electrons are accelerated in the waveguide, the electron beam path may be controlled by a suitable arrangement of steering magnets, or steering coils, which surround the waveguide. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide may be evacuated using a vacuum system comprising a vacuum pump or an arrangement of vacuum pumps. The pump system is capable of producing ultra-high vacuum (UHV) conditions in the waveguide and in the flight tube. The vacuum system also ensures UHV conditions in the electron gun. Electrons can be accelerated to speeds approaching the speed of light in the evacuated waveguide.

The radiation head 104 may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam. The X-rays may be filtered and may pass through one or more ion chambers for dose measuring. The radiation beam 122 can be shaped in various ways by beam-shaping apparatus 150, for example by using a multi-leaf collimator, before it passes into the subject as part of radiotherapy treatment.

In some implementations, the radiation head 104 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The radiotherapy device 100 may comprise a kV beam source and a kV detector or target. The kV beam source may be configured to emit or direct imaging radiation, for example X-rays, towards the subject. As the skilled person will appreciate, the kV beam source may be an X-ray tube or other suitable source of X-rays. The kV beam source is configured to produce kV energy radiation. Once the kV radiation has passed from the kV beam source and through the subject, the radiation continues towards kV detector. The kV detector may comprise or include an imaging panel. The kV detector may be configured to produce signals indicative of the intensity of radiation incident on the kV detector. In use, these signals are indicative of the intensity of radiation which has passed through the subject. These signals may be processed to form an image of the subject. This process may be described as the imaging apparatus and/or the kV detector capturing an image. The kV beam source and the kV detector may be fixed or attached to the gantry so that they are rotatable with the gantry, i.e. so that they rotate as the gantry rotates. By taking images at multiple angles around the subject it is possible to produce a 3D image of the patient, for example using tomographic reconstruction techniques.

The radiation head 104 and the kV beam source may be mounted on the gantry such that the radiation beam 122 emitted from the radiation head 104 travels in a direction that is generally perpendicular to that of the imaging beam emitted from the kV beam source.

As the skilled person will appreciate, the gantry 102 can be rotated to any of a number of angular positions relative to a patient. The radiation head 104 may direct radiation toward the subject at each or a number of these angular positions, according to a treatment plan. The gantry 102 may be configured to rotate to a number of discrete locations and/or to rotate continuously for a given time period. In other words, the gantry 102 can be rotated by 360 degrees around the subject, and in fact can continue to be rotated past 360 degrees. The radiation head 104 may be configured to irradiate the subject at the one or more of the discrete locations and/or to continuously irradiate the subject as it is rotated by the gantry 102. The angles from which radiation is applied, and the intensity and shape of the therapeutic beam, may depend on a specific treatment plan pertaining to a given subject.

The radiotherapy device 100 and/or the controller 140 may be configured to perform any of the method steps presently disclosed and may comprise computer executable instructions which, when executed by a processor cause the processor to perform any of the method steps presently disclosed, or when executed by the controller 140 cause the controller 140 to perform any of the method steps presently disclosed, or when executed by the radiotherapy device 100 cause the radiotherapy device 100 to perform any of the method steps presently disclosed. Any of the steps that the radiotherapy device 100 and/or the controller 140 is configured to perform may be considered as method steps of the present disclosure and may be embodied in computer executable instructions for execution by a processor. A computer-readable medium may comprise the above-described computer executable instructions.

The radiotherapy device 100 may be described as or comprise a linac. In some examples, the radiotherapy device 100 may be an MR-linac comprising an MR imaging apparatus configured to generate MR images of the subject. The MR imaging apparatus may be configured to obtain images of the subject positioned, i.e. located, on the support surface 110. The MR imaging apparatus may also be referred to as an MR imager. The MR imaging apparatus may be a conventional MR imaging apparatus operating in a known manner to obtain MR data, for example MR images. The skilled person will appreciate that such a MR imaging apparatus may comprise a primary magnet, one or more gradient coils, one or more receive coils, and an RF pulse applicator. The operation of the MR imaging apparatus is controlled by the controller 140. Alternatively or in addition to MR imaging, one or more other imaging techniques, modalities, sensors or detectors may be used, such as CT/X-ray, PET, optical imaging/cameras, infra-red imaging, ultra-sound imaging or time-of-flight techniques. Any one or more of these may be used before or during treatment of a subject.

The radiotherapy device 100 may also comprise several other components and systems as will be understood by the skilled person. For example, in order to ensure the linac does not leak radiation, appropriate shielding may also be provided. The radiotherapy device 100 is suitable for use with the techniques described in the present disclosure. One or more features of radiotherapy device 100 may be absent or altered according to particular requirements and particular implementations of the techniques of the present disclosure.

SGRT can improve the accuracy of radiotherapy treatment by verifying that the surface of the subject is in a position which reflects their position during a pre-treatment scan (e.g. a CT simulation). Since the pre-treatment scan data is what is used to determine how the dose will be deposited in the subject, verifying that the subject is in a corresponding position during treatment helps ensure that dose is applied in the intended anatomical locations. The present disclosure describes techniques for providing more accurate imaging of the surface of a subject and thereby to provide more accurate surface-guided radiotherapy and more accurate radiotherapy treatment. An improved distribution of cameras is described which enables increased accuracy of surface imaging in both a setup phase and a treatment phase. This is achieved while avoiding obstructing other components of the radiotherapy device or taking up valuable space in areas with tight space limitations.

Figure 2A:
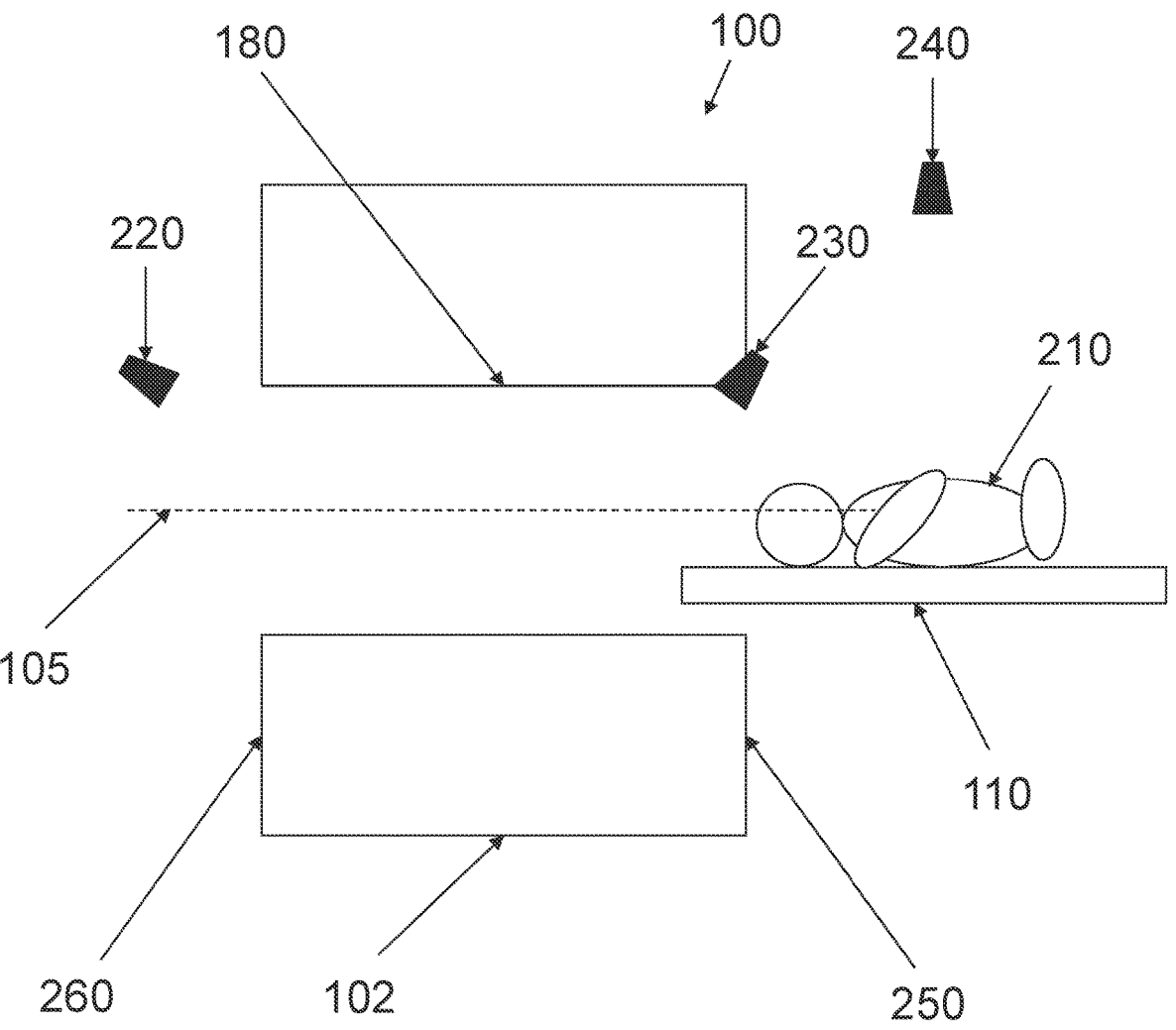
FIG. 2a depicts a further view of a radiotherapy device according to the present disclosure.
Figure 2B:
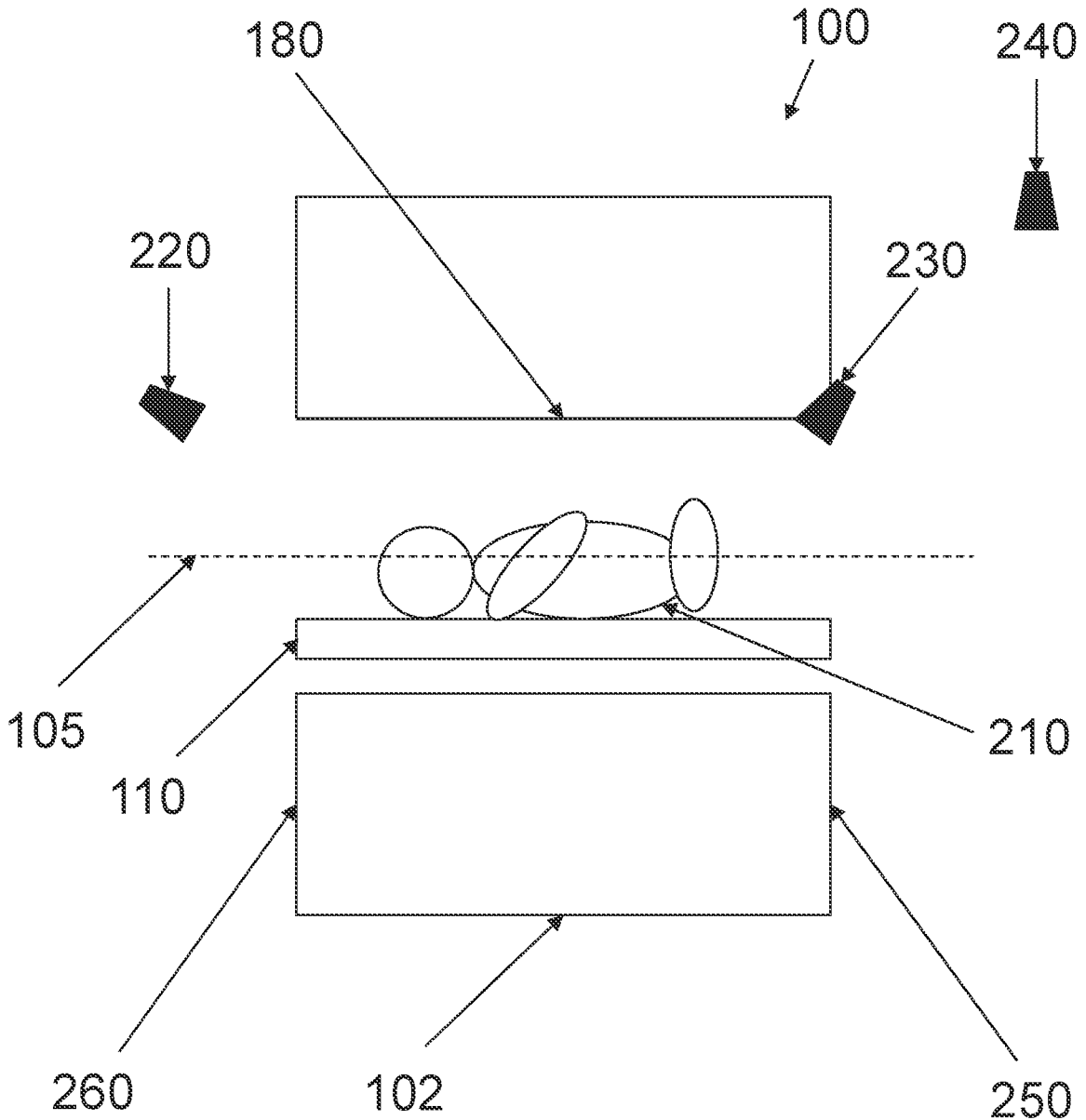
FIG. 2b depicts a further view of a radiotherapy device according to the present disclosure.

FIGS. 2*a* and 2*b* depict further views of a radiotherapy device 100 according to the present disclosure. The radiotherapy device 100 depicted in FIGS. 2*a* and 2*b* may correspond to the radiotherapy device 100 depicted in FIG. 1. Some features of the radiotherapy device 100 may be absent from FIG. 1 or FIG. 2*a* or FIG. 2*b* for ease of explanation of the arrangement of the depicted components.

FIG. 2*a* depicts a side view of the radiotherapy device 100. A subject 210 is positioned on the support surface 110. FIG. 2*a* may depict a setup phase in which the support surface 110 is positioned mostly or completely outside the bore 180 of the rotatable gantry 102. The axis of rotation 105 of the rotatable gantry is also depicted. The axis of rotation 105 may also be described as the central axis of the bore 180. In the setup phase, the subject 210 may be positioned in a suitable location on the support surface 110 for the radiotherapy treatment. It may be easier for the subject 210 to mount the support surface 110 with the support surface 110 positioned substantially outside the bore 180. The setup phase may involve positioning particular parts of the subject

110 in particular locations and/or at particular angles, in some cases with use of one or more accessories for assisting the subject 110 in taking up and maintaining a desired posture.

The rotatable gantry 102 may comprise a front 250 and a rear 260. For a substantially cylindrical radiotherapy device 100/bore 180, the front 250 of the rotatable gantry 102 may be substantially ring-shaped and the rear 260 of the rotatable gantry 102 may be substantially ring-shaped. The front 250 may be described as a front 250 of the radiotherapy device 100 or of the rotatable gantry 102. The rear 260 may be described as a rear 260 of the radiotherapy device 100 or of the rotatable gantry 102. The bore 180 may be described as a bore 180 of the radiotherapy device 100 or of the rotatable gantry 102.

The front 250 may be described as a front surface, a front side or a front face. In some examples, the front 250 may be substantially flat, i.e. be a front plane. In some examples, the front 250 may be curved and/or the transition between the front 250 and a portion of the radiotherapy device 100 extending substantially parallel to the bore 180 may be curved. The front 250 may be described as the frontmost portion of the radiotherapy device 100, i.e. the portion extending furthest towards the direction from which the support surface 110 enters the bore 180. Similarly, the rear 260 may be described as a rear surface, a rear side or a rear face. In some examples, the rear 260 may be substantially flat, i.e. be a rear plane. In some examples, the rear 260 may be curved and/or the transition between the rear 260 and a portion of the radiotherapy device 100 extending substantially parallel to the bore 180 may be curved. The rear 260 may be described as the rearmost portion of the radiotherapy device 100, i.e. the portion extending furthest towards the opposite direction to the direction from which the support surface 110 enters the bore 180, i.e. the portion extending furthest from the frontmost portion.

The front 250 corresponds to the side of the rotatable gantry 102 which the support surface 110 and/or the subject 210 enter and exit the bore 180 from. The main base of the support surface 110 is located to the side of the rotatable gantry 102 corresponding to the front 250. This is also the side where patient setup is performed. The rear 260 is the opposite surface of the rotatable gantry 102 to the front 250. The bore 180 may be accessible from the front 250 and may not be accessible, or at least not easily accessible, from the rear 260. The interior surface of the bore 180 may be perpendicular to the front 250 and the rear 260 and may connect the front 250 to the rear 260. In other words, the rotatable gantry 102, and/or the radiotherapy device 100, may be described as comprising a front 250, a rear 260 opposite the front, and a bore 180 between the front 250 and the rear 260.

FIG. 2*b* depicts the side view of the radiotherapy device 100 in a similar manner to FIG. 2*a*. In FIG. 2*b*, the subject 210 has been positioned inside the bore 180 of the rotatable gantry 102 by moving, e.g. translating, the support surface 110 into the bore 180. The support surface 110 has been moved parallel to the axis of rotation 105 in a direction oriented from the front 250 towards the rear 260. In other words, the support surface 110 has been moved into the bore 180 from a side of the radiotherapy device 100 corresponding to the front 250 of the rotatable gantry 102. FIG. 2*b* may depict a treatment phase in which the support surface 110 is positioned mostly or completely inside the bore 180 of the rotatable gantry. The treatment phase may occur subsequently to the setup phase, and may comprise radiotherapy treatment being delivered to the subject 210. The treatment phase thus may involve delivering a radiotherapy beam to irradiate and thereby treat one or more target regions in the subject.

As will be appreciated, the different locations of the subject 210 on the support surface 210 in FIGS. 2a and 2b may lead to suboptimal visibility of the subject 210 or parts thereof in one or both of the setup phase and the treatment phase. Techniques and arrangements for improving the positioning of cameras and optimising of the visibility of the subject 210 are set out below.

FIGS. 2a and 2b depict a plurality of cameras 220, 230, 240 of the radiotherapy device 100. The radiotherapy device 100 may be said to comprise the plurality of cameras 220, 230, 240 or may be said to be coupled to (e.g. communicatively coupled to) the plurality of cameras 220, 230, 240. The plurality of cameras 220, 230, 240 may be said to be associated with or disposed around or facing or viewing the radiotherapy device 100, or to be configured to be arranged in this manner. As used herein, a camera may also be referred to as a sensor or a detector and a plurality of cameras 220, 230, 240 may be referred to as a plurality of sensors or a plurality of detectors. The plurality of cameras 220, 230, 240 may be configured to monitor the position or location of the subject 210, or a part or surface thereof. The plurality of cameras 220, 230, 240 may be configured to enable or facilitate surface-guided radiotherapy.

The plurality of cameras 220, 230, 240 comprise a rear camera 220. The rear camera 220 may be positioned outside the bore 180 to the rear of the radiotherapy device 100, i.e. adjacent to the rear 260 of the rotatable gantry 102. The rear camera 220 may be oriented towards the rear 260 of the rotatable gantry 102/radiotherapy device 100. The rear camera 220 may be attached to a rear side of the radiotherapy device 100. In some examples, there may be several, e.g. two, three or four, rear cameras 220 positioned adjacent to the rear 260. In some examples, there may be an array of rear cameras 220 positioned adjacent to the rear 260. Use of multiple rear cameras 220 may increase the angles from which a subject can be viewed and thereby increase the number of surfaces and the number of points on those surfaces for which data is obtained. Data from multiple rear cameras 220 may be mapped onto each other and averaged in order to increase the accuracy of the acquired surface data. The rear camera 220 may be positioned vertically above the centre of the bore, i.e. vertically above the axis of rotation 105 of the rotatable gantry 102. The rear camera 220 may be arranged to be at a vertical height above the vertical height of a subject 210 on the support surface 110. The rear camera 220 may be disposed at a vertical height above the vertical height of the support surface 110. The rear camera 220 may be disposed at a vertical height level with the vertical height of the top of the bore 180. Alternatively, the rear camera 220 may be disposed at a vertical height below or above the height of the top of the bore 180. The rear camera 220 may be disposed at a vertical height below that of the vertical height of the top of the rotatable gantry 102. For a single rear camera 220, the rear camera 220 may be horizontally positioned level with the centre of the bore 180 (i.e. in the left-right direction). For multiple rear cameras 260, one or more of the rear cameras 260 may be positioned either side of the horizontal center of the bore 180. The one or more rear cameras 220 may be oriented to coincide with the centre of the bore 180/with the radiation isocentre.

The plurality of cameras 220, 230, 240 may comprise one or more near-bore cameras 230. The one or more near-bore cameras 230 may be located on, at or close to the front 250 of the rotatable gantry 102. The one or more near-bore cameras 230 may be located at a transition point or in a transition region or in a curved region or at an angle between the front 250 and the interior of the bore 180. The one or more near bore cameras 230 may be attached to a front side of the radiotherapy device 100. In some examples, the one or more near-bore cameras 230 may be located inside the bore 180 proximal to the front 250 of the rotatable gantry 102. The one or more near-bore cameras 230 may be arranged to be at a vertical height above the vertical height of a subject 210 on the support surface 110. The one or more near-bore cameras 230 may disposed at a vertical height above the vertical height of the axis of rotation of the radiotherapy device 100. The one or more near-bore cameras 230 may be disposed at a vertical height between the vertical height of the support surface 110 and the vertical height of the top of the bore 180, or at the same vertical height as the top of the bore 230. The one or more near-bore cameras 230 may be disposed, for example, in a top half, third, quarter, fifth, tenth, or twentieth of the vertical extent of the bore 180. In the side view depicted in FIGS. 2a and 2b, only one near-bore camera 230 may be visible. One or more additional near-bore cameras 230 may be located behind the visible near-bore camera 230 from the perspective shown in FIGS. 2a and 2b. The one or more near-bore cameras 230 may be oriented to coincide with the centre of the bore 180/with the radiation isocentre.

The plurality of cameras 220, 230, 240 may comprise one or more setup cameras 240. The one or more setup cameras 240 may be located close to or adjacent to the front 250 of the rotatable gantry 102. The one or more setup cameras 240 may be located on the side of the radiotherapy device 100 corresponding to the front 250 of the rotatable gantry 102, i.e. closer to the front 250 than the rear 260. The one or more setup cameras 240 may be oriented vertically downwards or may be oriented at least partially towards the front 250 of the rotatable gantry 102, e.g. at an angle between vertically downwards and the axis of rotation running from the front 250 to the rear 260. The one or more setup cameras 240 may be configured to view the subject 210 in the setup position, i.e. with the support surface 110 withdrawn from the bore 180. The one or more setup cameras 240 may be separated from the front 250 by a distance greater than the distance between the rear camera 220 and the rear 260. The one or more setup cameras 240 may be separated from the one or more near-bore cameras 230 by a distance greater than any distance separating the one or more near-bore cameras 230 and the front 250 of the rotatable gantry 102. The one or more setup cameras 240 may be disposed at a vertical height higher than the top of the bore 180. The one or more setup cameras 240 may be disposed at a vertical height level with a part (e.g. a top arc) of the rotatable gantry 102 or higher than the top of the rotatable gantry 102. The one or more setup cameras 240 may be oriented to coincide with the centre of the bore 180/with the radiation isocentre. In the side view depicted in FIGS. 2a and 2b, only one setup camera 240 may be visible. One or more additional setup cameras 240 may be located behind the visible setup camera 240 from the perspective shown in FIGS. 2a and 2b. While these cameras are referred to as 'setup cameras' 240, it will be appreciated that they may be dedicated to setup, but also be used when the support surface 110 and the subject 210 are within the bore 180, e.g. during treatment, such as to image the parts of the surface which are not visible for the rear camera 220 and/or the near-bore cameras 230.

One or more of the plurality of cameras 220, 230, 240 may be configured to be fixed or supported in various ways (e.g. using mounting means), for example fixed to the ceiling of the room containing the radiotherapy device 100, fixed to a free-standing support, fixed to the rotatable gantry 102 or fixed to an additional gantry or rig of the radiotherapy device 100. The one or more near-bore cameras 230 may be fixed to a front side of the radiotherapy device 100, e.g. to an additional gantry or rig of the radiotherapy device 100. The one or more setup cameras 240 may be fixed to the ceiling of the room containing the radiotherapy device 100. The rear camera 220 may be fixed to the radiotherapy device 100 via mounting means, e.g. via one or more rods, arms and/or clamps. This may enable the mounting means to be relatively short, which may increase stability and reduce engineering complexity and cost.

Figure 3:
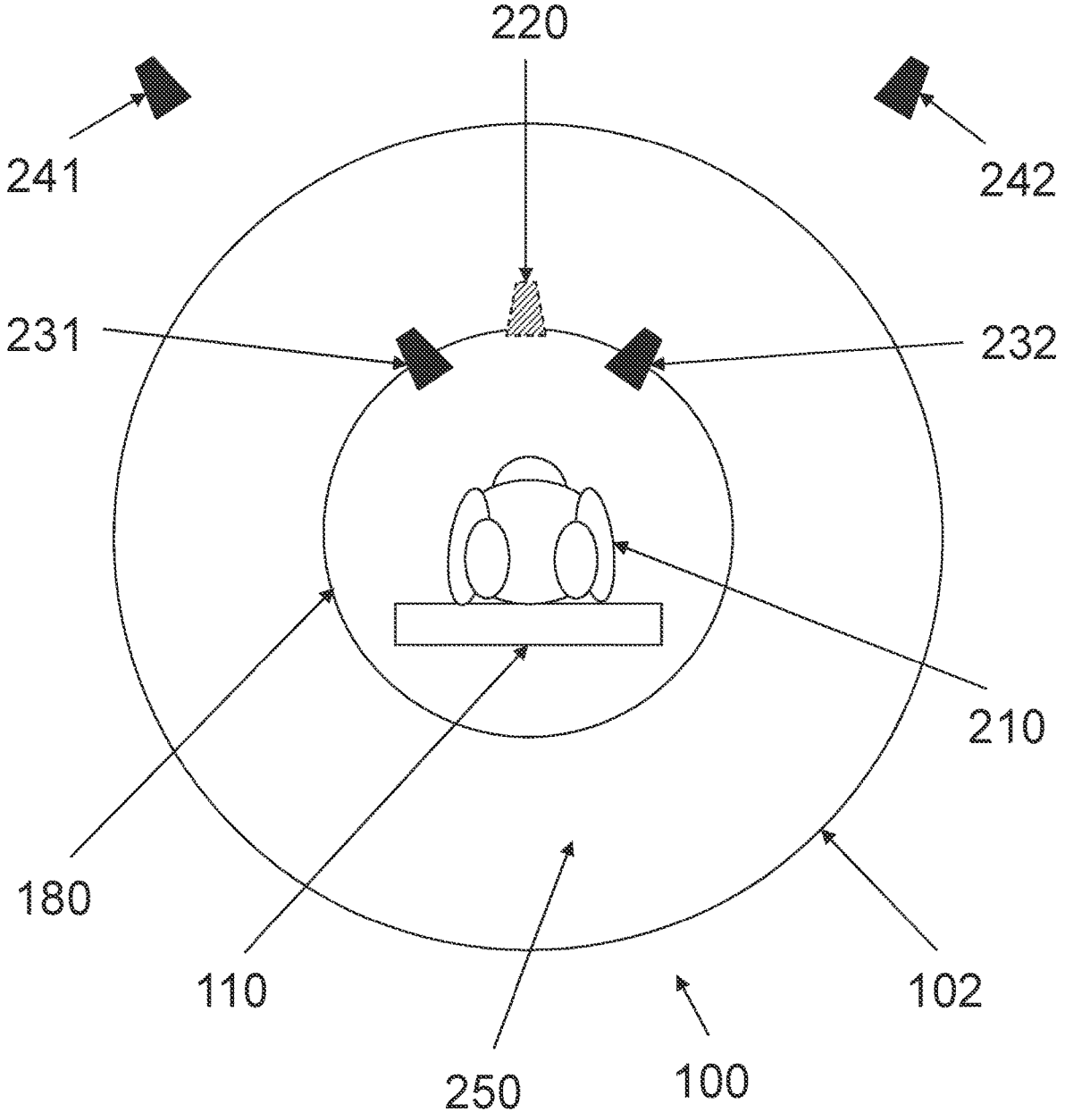
FIG. 3 depicts a further view of a radiotherapy device according to the present disclosure.

FIG. 3 depicts a further view of a radiotherapy device 100 according to the present disclosure. FIG. 3 depicts the radiotherapy device 100 from its front side, i.e. from a perspective looking along the axis of rotation 105 of the rotatable gantry 102 and facing the front 250 of the rotatable gantry 102. The subject 210 is positioned on the support surface 110 in or close to the bore 180 of the rotatable gantry 102.

FIG. 3 provides an additional view of the plurality of cameras 220, 230, 240 discussed in relation to FIGS. 2a and 2b. The rear camera 220 is depicted with dotted lines and shading to indicate that it is located (at least partially) behind the radiotherapy device 100 from the perspective shown in FIG. 3. This is because the perspective shown in FIG. 3 is facing the front 250 of the rotatable gantry 102 and the rear camera 220 is adjacent to the rear 260 of the rotatable gantry 102.

FIG. 3 also depicts a first near-bore camera 231 and a second near-bore camera 232. These may correspond to the one or more near-bore cameras 230 of FIGS. 2a and 2b. The first near-bore camera 231 and the second near-bore camera 232 may be located at the same vertical height. The first near-bore camera 231 and the second near-bore camera 232 may be located horizontally adjacent to each other, i.e. with a certain horizontal (left-right) separation. The first near-bore camera 231 may be oriented towards the centre of the bore 180 along a horizontal direction and the second near-bore camera 232 may be oriented towards the centre of the bore 180 along the horizontal direction. In other words, the views of the first near-bore camera 231 and the second near-bore camera 232 may intersect (in the horizontal direction). This may provide views of the subject 210 from opposing horizontal directions, thereby providing a more complete view of the surfaces of the subject 210.

FIG. 3 also depicts a first setup camera 241 and a second setup camera 242. These may correspond to the one or setup cameras 240 of FIGS. 2a and 2b. The first setup camera 241 and the second setup camera 242 may be located at the same vertical height. The first setup camera 241 and the second setup camera 242 may be located horizontally adjacent to each other, i.e. with a certain horizontal (left-right) separation. The horizontal separation of the first setup camera 241 and the second setup camera 242 may be greater than the horizontal separation between the first near-bore camera 231 and the second near-bore camera 232. The first setup camera 241 may be oriented towards the centre of the bore 180 along a horizontal direction and the second setup camera 242 may be oriented towards the centre of the bore 180 along the horizontal direction. In other words, the views of the first near-bore camera 231 and the second near-bore camera 232 may intersect (in the horizontal direction). This may provide views of the subject 210 from opposing horizontal directions, thereby providing a more complete view of the surfaces of the subject 210.

The arrangement of the plurality of cameras 220, 230, 240 depicted in FIGS. 2a, 2b and 3 is provided as an example. In some examples, one or more of the plurality of cameras 220, 230, 240 may be absent or may have a different location and/or orientation relative to that depicted in these Figures. In some examples, one or more additional cameras may be present in the arrangement.

The inventors have identified that the arrangement of the plurality of cameras 220, 230, 240 depicted in FIGS. 2a, 2b and 3 has several advantages. The visibility of the subject 210 is maximised in both setup and treatment phases even with the obstruction to lines of sight caused by the radiotherapy device 100 being a bore-based machine. The use of a bore 180 as described in the current disclosure is advantageous because it can protect the patient from colliding with the rotatable gantry 102, which is particularly important for higher rotation speeds of the rotatable gantry 102. The positioning of the rear camera 220 may not be needed, appropriate or considered for non-bore-based radiotherapy devices, for example those for which the treatment head is disposed on an arm protruding from the gantry. For such a radiotherapy device, there is no bore to obstruct the lines of sight from cameras facing the front of the radiotherapy device such that additional cameras may not be considered. Moreover, parts of such a radiotherapy device may block the field of view from any camera positioned to the rear of the radiotherapy device such that implementation of a rear camera would not be considered.

The arrangement of the plurality of cameras 220, 230, 240 enables accurate determination of the surface shape and position of the subject 210 both before the treatment begins for the purposes of arranging the subject 210 in a desired manner and during the treatment to ensure that the subject 210 is in a suitable position such that radiotherapy will be applied to the intended anatomical locations within the subject 210.

The rear camera 220 increases the volume imaged and in particular provides surface information for parts of the subject 220 'deep into the bore', i.e. towards the rear 260 of the rotatable gantry 102. In some examples, the subject 210 may be treated 'head-first', i.e. with their head located closer to the rear 260 than the front 250 (as depicted in FIGS. 2a, 2b and 3). The rear camera 220 may then provide additional or more accurate data regarding the head and upper body of the subject 210 since it is located closer to and in general at a less shallow angle to the surface of the subject 210. In other examples, the subject 210 may be treated 'feet-first', i.e. with their head closer to front 250 than rear 260. The rear camera 220 may then provide additional or more accurate data regarding the lower body of the subject 210. The positioning of the rear camera 220, and the combination of this with the other cameras 230 and 240 of the plurality of cameras, may enable increased versatility of treatments through providing accurate imaging capable of monitoring the subject 210 during both head-first and feet-first treatments.

It is desirable for the bore 180 of the radiotherapy device 100 to be able to accommodate subjects 210 of various different sizes and shapes. As such, the space inside the bore is limited. Increasing the size of the bore would require a larger and more expensive rotatable gantry 102. Cameras inside the bore may obstruct the subject 210 or other components of the radiotherapy device 100 or the delivery of radiotherapy. They may also be more liable to being damaged. Cameras inside the bore diminish the bore diameter at the points where the cameras are located. In addition, the absolute accuracy of such cameras inside the bore can have poor absolute accuracy since the inside of the bore may move. This may limit the ability to provide accurate absolute position measurements. According to the present disclosure, the rear camera 220 is advantageously located outside the bore 180, while still being able to view well into the interior of the bore 180, in particular being able to view locations in the interior of the bore 180 that are less visible or not visible using the one or more near-bore cameras 230 and/or the one or more setup cameras 240 located closer to the front 250. This positioning of the rear camera 220 enables more space inside the bore 180 to be freed up and enables more accurate absolute position measurements to be achieved.

The one or more near-bore cameras 230 may be disposed at or close to the front 250 such that they can view into the bore 180 so as to provide data regarding the surface of the subject 210 during treatment. The one or more near-bore cameras 230 may be positioned close to but outside the bore 180, e.g. at a transition point or in a transition region between the interior of the bore 180 and the front 250. This avoids taking up space inside the bore, while being close enough and at an angle to the surface normal of the subject 210 suitable for providing accurate and useful data.

The location of the one or more near-bore cameras 230 may be close to but outside the bore 180, meaning in general that the near-bore cameras 230 are slightly further from the subject 210 than they would be if they were located inside the bore 180. This is beneficial since the cameras should preferably not be used to image surfaces less than 0.3 m away to prevent accuracy degrading. In addition, for a given field of view of camera, it may be easier to view the full extent of the subject 210 with the one or more near-bore cameras 230 located close to but outside the bore 180 since they are able to view down the length of the subject 210. Moreover, the location of the one or more near-bore cameras 230 outside the bore 180 enables more space for them to be installed and/or serviced and avoids potential issues relating to locating them so as to bypass the rotation of the rotatable gantry 102.

Views from the rear camera 220 and the one or more near-bore cameras 230 may be mapped onto each other, combined, correlated or averaged. The location of the one or more near-bore cameras 230 outside the bore 180, as opposed to inside the bore 180, enables better 'teamwork' between the one or more near-bore cameras 230 and the rear camera 220. Since the first near-bore camera 231 and the second near-bore camera 232 may be positioned horizontally spaced from one another, away from the horizontal centre of the bore 180, they may view the isocentre and/or surfaces of the subject 210 from different horizontal angles to each other and a different horizontal angle to the rear camera 220 (which may be centred horizontally relative to the bore 180). This combination of camera positioning therefore enables views of the subject 210 from more directions, which increases the visibility of the different surfaces of the subject 210.

The one or more setup cameras 240 are suitably located to view the subject 210 in a setup phase for which the support surface 210 is predominantly outside the bore 180. The one or more setup cameras 240 may be disposed at a vertical height above the vertical height of the top of the rotatable gantry 102, for example may be fixed to the ceiling of the room containing the radiotherapy device 100. This may provide a location of the one or more setup cameras 240 which is relatively far removed from the surface of the subject 210. With this arrangement, the distance between each point on the surface of the subject 210 and a setup camera 240 may be fairly similar, in relative terms to the distance between each other point on the surface of the subject 210 and the setup camera 240. In other words, a distance between the closest point on the surface of the subject 210 and the setup camera 240 may be fairly similar to a distance between the furthest point on the surface of the subject 210 and the setup camera 240 when considered relative to the average distance between points on the surface of the subject 210 and the setup camera 240. This may advantageously provide more uniform point density of the data obtained and reduce the risk of severe deformations in the captured surface data.

In comparing the views of different cameras of the plurality of cameras 220, 230, 240, the coordinate systems of the different cameras may be mapped onto each other. Locations inside the bore 180 and locations outside the bore 180 may be mapped onto the same coordinate system. The coordinate system of the room may be used as the reference coordinate system and the respective coordinate systems of each of the plurality of cameras 220, 230, 240 may be mapped onto that reference coordinate system. The coordinate systems of one of the plurality of cameras 220, 230, 240 may be used as the reference coordinate system and the data and coordinate systems of the other cameras of the plurality of cameras 220, 230, 240 may be mapped onto that reference coordinate system. The locations and angles of each of the plurality of cameras 220, 230, 240, for example relative to the coordinate system of the room, may be known or measured and used to geometrically map between coordinate systems. The data obtained by the plurality of cameras may be calibrated in order to indicate the location of the surface of the subject 210 in the reference coordinate system.

The views of one or more cameras of the plurality of cameras 220, 230, 240 may overlap with the views of one or more other cameras of the plurality of cameras 220, 230, 240. In other words, for a first camera of the plurality of cameras 220, 230, 240 arranged to image a first series of surfaces and a second camera of the plurality of cameras 220, 230, 240 arranged to image a second series of surfaces, a subset of the first series of surfaces may be the same as a subset of the second series of surfaces. Different cameras of the plurality of cameras 220, 230, 240 may view the same surface(s) from different respective angles. For example, the view of the first setup camera 241 may overlap with the view of the second setup camera 242. The view of the first near-bore camera 231 may overlap with the view of the second near-bore camera 232. The views of one or more of the setup cameras 240 may overlap with the views of one or more of the near-bore cameras 230. The views of one or more of the near-bore cameras 230 may overlap with the view of the rear camera 220.

The overlap of the views of cameras of the plurality of cameras 220, 230, 240 advantageously enables increased accuracy in the determination of a location of a surface imaged by multiple cameras. For example, the location of a surface of the subject 210 determined from a first camera may be averaged with the location of the surface of the subject 210 determined from a second camera. This may further reduce the error with which the location of the surface is known.

The plurality of cameras 220, 230, 240 may implement any imaging modality suitable for measuring a surface of the subject 210, including those using 2D cameras/technologies and/or 3D cameras/technologies. Any one or more (up to and including all) of the plurality of cameras 220, 230, 240 may comprise a visible light camera (e.g. a 2D RGB camera), a structured light camera, a LIDAR camera, a stereo vision camera, a time of flight camera, a structured light camera or a laser range scanner, as would be understood by the skilled person in the relevant technical field.

A time of flight camera measures the distance between the camera and a surface by illuminating the surface with a light pulse and detecting the time taken for the reflected light pulse to return to the camera. A time of flight camera thus comprises an illumination unit, such as an LED or a laser diode, configured to generate and emit light pulses. These light pulses may, for example, be of infrared light. A time of flight camera also comprises optics and an image sensor configured to receive the light pulse reflected from the surface and to measure the round-trip time taken for the light pulse to return to the camera. While some time of flight technologies focus on individual pulses of light, others work on the continuous wave principle where pulses of light are emitted continuously (forming a type of square wave) during a frame (image) acquisition at a very high frequency. This allows for looking at the time shift of the whole signal, rather than the individual pulses, known as phase-shift. The returning light may be band-pass filtered in order to filter out frequencies not corresponding to the frequencies of the emitted light pulse, which may reduce the noise of the obtained signal. This can be performed based on knowing the exact frequency of the pulse wave. This enables avoidance of some external noise, as well as light signals from other cameras running in parallel which may have been configured with a slightly different frequency (known as frequency modulation).

The light pulse travels to a surface a distance d away at the speed of light c, i.e. approximately $3\times10^8$ ms$^{-1}$. The time t taken for the light pulse to return is equal to 2*d/c. Thus, by measuring the time t taken for the light pulse to return, the distance d to the surface can be calculated as c*t/2. Since the speed of light is very fast, for distances d of the order of a meter, the time t is of the order of several nanoseconds. Accurate synchronisation of the illumination unit and the image sensor is required to measure these times, which may be achieved using driver electronics transmitting high speed signals to these components.

In a laser scanning array, the light source may be scanned to illuminate a range of different points on a surface in turn. In contrast, time of flight imaging may use a single light pulse to generate 3D surface information. This may be referred to as direct time of flight imaging. The image sensor of the time of flight camera may comprise a focal plane array configured to detect photons at the wavelength of the emitted (and reflected) light pulse at each of an array of pixels (and at a range of other nearby wavelengths). Photodiodes may be used to generate respective electrical charges proportional to the number of photons detected at each pixel. Each of the pixels may correspond to a different point on the imaged surface. The electrical charges for different pixels will be generated at different times depending on the round-trip time of the light pulse to different points on the imaged surface. Thus, the distance from the camera to each point on the imaged surface can be obtained at high speed to provide real-time imaging. This can be used to monitor the position of a subject 210 in real-time during setup and/or treatment.

While time of flight cameras are low-cost relative to typical SGRT cameras, their limited accuracy has previously limited their use for radiotherapy applications. Improvements in the accuracy of these devices and improvements in the processing of the data acquired as described below make implementation into radiotherapy devices more possible and more advantageous. In particular, when using time of flight imaging for radiotherapy, the distance measurement associated with a particular pixel may not be as accurate as desired. In other words, the distance between the camera and a particular point on the surface of the subject 210 may not be known as accurately as desired, i.e. it may have a significant associated error. To address this, an average may be taken over several pixels, i.e. over several points on the surface of the subject 210. (Alternatively, or in addition, an average may be taken over several temporal frames.) The average may be determined by the respective camera or by the controller 140. The error associated with the averaged value will then be lower than the error associated with any particular point on the surface. In other words, a certain degree of spatial resolution may be sacrificed in order to obtain a more accurate distance measurement to a region of the surface comprising several individual points. A series of surface measurements can thereby be obtained which are accurate enough for setup positioning and real-time monitoring of a subject 210 during radiotherapy treatment.

In order to calculate an average over a plurality of points on the surface of the subject 210, it is desirable that the angle between a particular surface and the viewing direction of the time of flight camera is not too shallow. In other words, it is desirable that the angle between the surface and the viewing direction of the time of flight camera is closer to perpendicular rather than close to parallel. With this geometry, for a given density of imaged points, the surface will coincide with a greater number of those points such that spatial averaging can be used to determine a more accurate averaged distance to the surface.

In the arrangement shown in FIGS. 2a, 2b and 3, one, multiple, or all of the plurality of cameras 220, 230, 240 may be a time of flight camera. It can be seen that the lateral distance (along the axis of rotation 105) between the one or more near-bore cameras 230 and the head of the subject 210 is rather large, such that, with the support surface 110 within the bore 180, the one or more near-bore cameras 230 may view the head of the subject 210 at a rather shallow angle. As described herein, a rear camera 220 may be provided. The angle between the parts of the subject 210 disposed towards the left of FIG. 2b and the viewing direction of the rear camera 220 is less shallow than that between these same parts of the subject 210 and the one or more near-bore cameras 230. Therefore, spatial averaging of the surface information obtained from the rear camera 220 may be better enabled for these parts of the subject 210 such that the locations of these parts of the surface of the subject 210 may be obtained more accurately with the addition of the rear camera 220.

While the subject is depicted as entering the bore 'head-first' in FIGS. 2a, 2b and 3, it will be understood that corresponding benefits apply for 'feet-first' treatments in respect of the lower parts of the subject 210. The combination of the different positions of the plurality of cameras 220, 230, 240 enables more accurate imaging of the different parts of the subject in both the setup phase and the treatment phase. This geometrical arrangement may be particularly important for time of flight imaging due to the above-described spatial averaging which may be performed to increase the distance accuracy of this imaging modality. Therefore, the combination of time of flight imaging and the arrangement of one or more of the plurality of cameras 220, 230, 240, e.g. of the rear camera 220, may be particularly advantageous.

In some examples, the radiotherapy device 100 may comprise a (single) overhead projector, or multiple overhead projectors, which may be fixed to the ceiling of the room containing the radiotherapy device 100 or to the radiotherapy device 100 itself. The projector may be communicatively coupled to one or more of the plurality of cameras 220, 230, 240 and/or to the controller 140. The projector may, for example, be configured to illuminate the subject 210 or parts thereof during the setup phase. The controller 140 may determine that one or more parts of the subject 210 are not in an intended position by comparing the surface locations obtained from one or more of the plurality of cameras 220, 230, 240 with reference positions, for example based on a treatment plan. The projector may illuminate the one or more parts of the subject 210 to inform a clinician that these one or more parts need to be re-positioned before treatment. This projector may differ from projectors included when implementing structured light technology, which project a grid onto the subject 210 to facilitate measurement of the surface and for which each camera has its own projector.

While much of the discussion above has focused on determining the locations of surfaces of a subject 210, the apparatus and techniques described herein can alternatively or additionally be used to determine the locations of one or more components of the radiotherapy device 100 and/or other equipment within the room containing the radiotherapy device 100. For example, one or more of the plurality of cameras 220, 230, 240 may be used to monitor or determine the location of the support surface 210.

A radiotherapy apparatus may be described as comprising a radiotherapy device and a plurality of cameras as described herein. The radiotherapy device as described herein may comprise a front, a rear and a bore. The radiotherapy device may comprise a rotatable gantry as described herein and a support surface as described herein moveable into the bore from the front of the radiotherapy device. The plurality of cameras may be for monitoring a subject that is located on the support surface, and may comprise a rear camera as described herein disposed adjacent to the rear of the radiotherapy device.

FIG. 4 depicts a method for imaging a subject according to the present disclosure.

In a step 402, a subject 210 may be disposed on the support surface 110 of the radiotherapy device 100. For example, the subject 210 may lie on the support surface 210, be arranged in a particular pose and/or be positioned with respect to one or more markers. The support surface 110 may be withdrawn from, i.e. mostly or completely outside, the bore 180 of the rotatable gantry 102 when the subject 210 mounts the support surface 110 (i.e. during setup and positioning of the subject 210) for ease of access.

In a step 404, one or more images of the subject 210 may optionally be obtained using one or more cameras of the plurality of cameras 220, 230, 240 of the radiotherapy device. The one or more images may be obtained with the support surface 110 withdrawn from, i.e. mostly or completely outside, the bore 180 of the rotatable gantry 102, for example using the one or more setup cameras 240. The one or more images may be used to position the subject 210, to check whether the subject 210 is in the desired position, and/or to reposition the subject 210. This may correspond to the setup phase.

In a step 406, the support surface 110 may be moved into the bore 180 of the rotatable gantry 102 of the radiotherapy device 100 from a side of the radiotherapy device 100 corresponding to a front 250 of the rotatable gantry 102. In other words, the interior of the bore 180 may be accessible from the side of the radiotherapy device 100 corresponding to the front 250. The interior of the bore 180 may not be accessible, at least not easily accessible, from the side of the radiotherapy device 100 corresponding to the rear 260. The subject 210 may be disposed on the support surface 110 as it moves into the bore 180. The support surface 110 may be moved, e.g. translated, using one or more motors and/or one or more actuators. This movement may be controlled by the controller 140 of the radiotherapy device 100.

In a step 408, one or more images of the subject 210 may be obtained using a rear camera 240 of the plurality of cameras 220, 230, 240, the rear camera being disposed adjacent to a rear 260 of the rotatable gantry 102. The rear 260 may be opposite to the front 250, i.e. may be at the opposite side of the bore 180 to the front 250. The one or more images may be obtained immediately after movement of the support surface 210 into the bore 180, i.e. without a treatment or before a treatment starts, to determine whether the subject 210 is in the desired position when moved into the bore 180. The one or more additional images may be obtained during a treatment to determine whether the subject 210 is in a desired position in real-time to indicate whether the intended dose is being delivered to the intended regions and whether the treatment should continue.

While the methods disclosed herein are presented in a certain sequential order, this should not be taken to limit the methods to the orders presented. One or more of the method steps may be omitted or rearranged. The various steps may be performed in different orders. Various steps may be performed at the same time or substantially the same time. Herein, references to events occurring substantially at the same time may refer to events at least partially overlapping in time and/or events occurring at the same time within measurement uncertainties.

Figure 5:
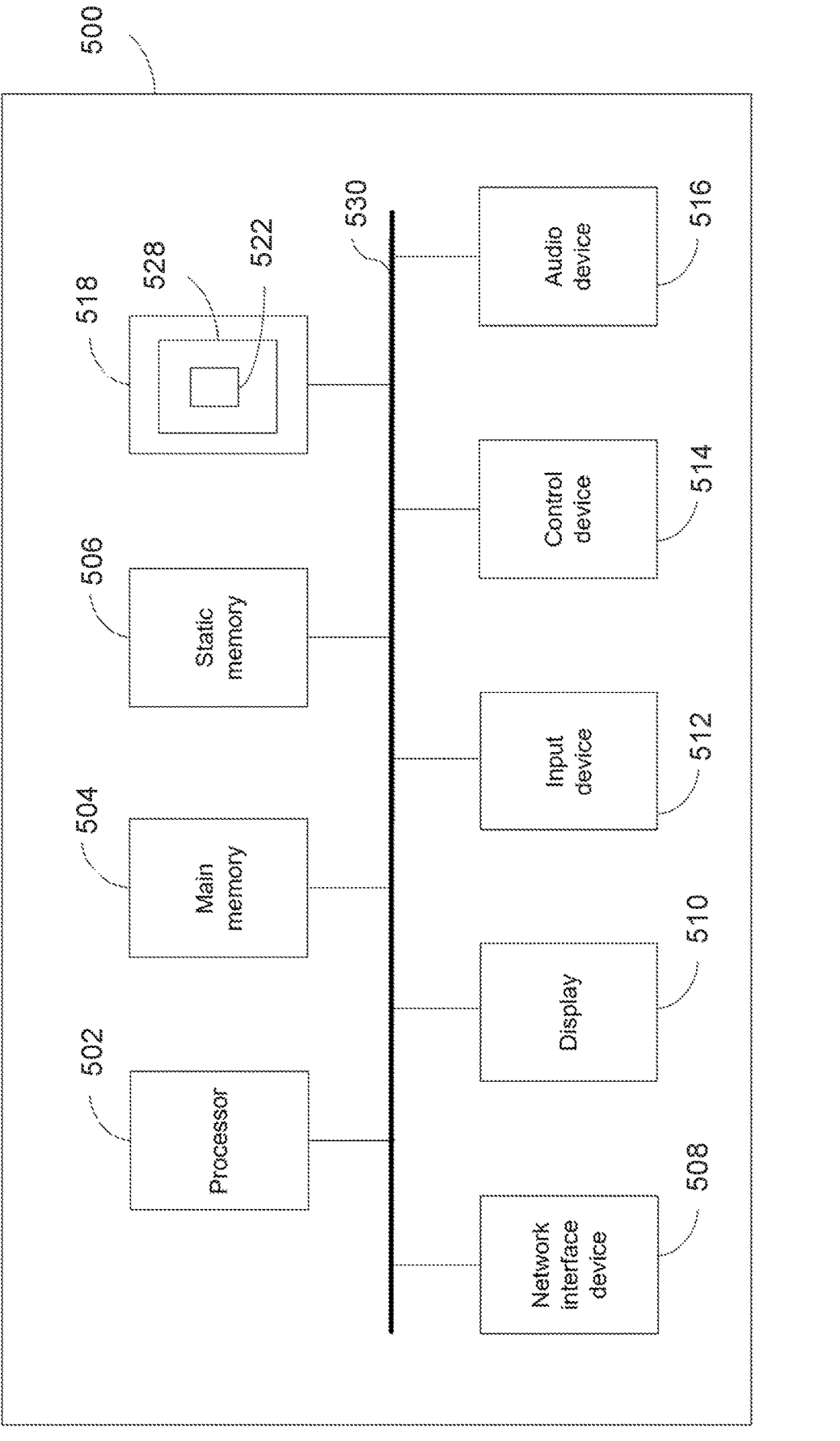
FIG. 5 depicts an example implementation of a computing device according to the present disclosure.

FIG. 5 illustrates a block diagram of one implementation of a computing device 500 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein. The computing device 500 may correspond to any one or more of the controllers or control devices described herein. The computing device 500 may control movement of the support surface 210 and/or may control operation of one or more cameras of the plurality of cameras 220, 230, 240 as described herein. Data from one or more of the plurality of cameras 220, 230, 240 may be transmitted to the computing device 500 and the computing device 500 may determine the location of one or more surfaces of the subject 210 based on this data.

The example computing device 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a secondary memory (e.g., a data storage device 518), which communicate with each other via a bus 530.

Processing device 502 represents one or more general-purpose processors such as a microprocessor, central processing unit, or the like. More particularly, the processing device 502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. Processing device 502 is configured to execute the processing logic (instructions 522) for performing the operations and steps discussed herein.

The computing device 500 may further include a network interface device 508. The computing device 500 also may include a video display unit 510 (e.g., a liquid crystal display (LCD) or a cathode ray tube (CRT)), an alphanumeric input device 512 (e.g., a keyboard or touchscreen), a cursor control device 514 (e.g., a mouse or touchscreen), and an audio device 516 (e.g., a speaker).

The data storage device 518 may include one or more machine-readable storage media (or more specifically one or more non-transitory computer-readable storage media) 528 on which is stored one or more sets of instructions 522 embodying any one or more of the methodologies or functions described herein. The instructions 522 may also reside, completely or at least partially, within the main memory 504 and/or within the processing device 502 during execution thereof by the computer system 500, the main memory 504 and the processing device 502 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hardwired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," "applying," "transmitting," "generating," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The approaches described herein may be embodied on a computer-readable medium, which may be a non-transitory computer-readable medium. The computer-readable medium may carry computer-readable instructions arranged for execution upon a processor so as to cause the processor to carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The disclosure comprises the following items:

1. A radiotherapy device comprising:

a rotatable gantry comprising a front, a rear and a bore;

a support surface moveable into the bore from a side of the radiotherapy device corresponding to the front of the rotatable gantry; and a plurality of cameras for monitoring a subject that is located on the support surface, the plurality of cameras including a rear camera disposed adjacent to the rear of the rotatable gantry.

2. A radiotherapy device according to item 1, wherein the rear camera is disposed at a vertical height above the vertical height of the support surface, and/or wherein the rear camera is disposed at a vertical height above the vertical height of the central axis of the bore.

3. A radiotherapy device according to item 1 or item 2, wherein the plurality of cameras comprise one or more near-bore cameras disposed on or adjacent to the front of the rotatable gantry or disposed on or adjacent to an interior of the bore proximal to the front of the rotatable gantry.

4. A radiotherapy device according to item 3, wherein the one or more near-bore cameras are disposed at a vertical height above the vertical height of the support surface and below the vertical height of the top of the radiotherapy device.

5. A radiotherapy device according to item 3 or item 4, wherein the one or more near-bore cameras comprise a first near-bore camera disposed towards a left edge of the bore relative to the central axis of the bore, and a second near-bore camera disposed towards a right edge of the bore relative to the central axis of the bore.

6. A radiotherapy device according to any preceding item, wherein the plurality of cameras comprise one or more setup cameras disposed outside the bore and located on the side of the radiotherapy device corresponding to the front of the rotatable gantry.

7. A radiotherapy device according to item 6, wherein the one or more setup cameras are disposed at a vertical height above the vertical height of the top of the bore.

8. A radiotherapy device according to item 6 or item 7, wherein the one or more setup cameras comprise a first setup camera disposed to the left of the bore relative to the central axis of the bore, and a second setup camera disposed to the right of the bore relative to the central axis of the bore.

9. A radiotherapy device according to any of items 6-8, wherein at least the one or more setup cameras are arranged to view the subject in a setup position in which most or all of the support surface is outside of the bore.

10. A radiotherapy device according to any of items 3-5, wherein at least the rear camera and the one or more near-bore cameras are arranged to view the subject in a treatment position in which most or all of the support surface is inside of the bore.

11. A radiotherapy device according to any preceding item, wherein one or more of the plurality of cameras is a time of flight camera.

12. A radiotherapy device according to item 11, wherein each time of flight camera is configured to determine a spatial average of a plurality of pixels, each of the plurality of pixels corresponding to a respective distance measurement to a respective point on the surface of the subject.

13. A method for imaging a subject using a radiotherapy device comprising a rotatable gantry, a support surface, and a plurality of cameras, the method comprising:

moving the support surface with the subject disposed thereon into a bore of the rotatable gantry from a side of the radiotherapy device corresponding to a front of the rotatable gantry; and obtaining one or more images of the subject using a rear camera of the plurality of cameras, the rear camera being disposed adjacent to a rear of the rotatable gantry.

14. A method according to item 13, further comprising, with the subject disposed on the support surface and before moving the support surface into the bore, obtaining one or more further images of the subject using one or more cameras of the plurality of cameras.

15. A method according to item 13 or item 14, wherein the rear camera is disposed at a vertical height above the vertical height of the support surface, and/or wherein the rear camera is disposed at a vertical height above the vertical height of the central axis of the bore.

16. A method according to any of items 14-15, wherein the plurality of cameras comprise one or more near-bore cameras disposed on or adjacent to the front of the rotatable gantry or disposed on or adjacent to an interior of the bore proximal to the front of the rotatable gantry.

17. A method according to item 16, wherein the one or more near-bore cameras are disposed at a vertical height above the vertical height of the support surface and below the vertical height of the top of the radiotherapy device.

18. A method according to item 16 or item 17, wherein the one or more near-bore cameras comprise a first near-bore camera disposed towards a left edge of the bore relative to the central axis of the bore, and a second near-bore camera disposed towards a right edge of the bore relative to the central axis of the bore.

19. A method according to any of items 13-18, wherein the plurality of cameras comprises one or more setup cameras disposed outside the bore and located on the side of the radiotherapy device corresponding to the front of the rotatable gantry.

20. A method according to item 19, wherein the one or more setup cameras are disposed at a vertical height above the vertical height of the top of the bore.

21. A method according to item 19 or 20, wherein the one or more setup cameras comprise a first setup camera disposed to the left of the bore relative to the central axis of the bore, and a second setup camera disposed to the right of the bore relative to the central axis of the bore.

22. A method according to any of items 19-21, wherein at least the one or more setup cameras view the subject in a setup position in which most or all of the support surface is outside of the bore.

23. A method according to any of items 16-18, wherein at least the rear camera and the one or more near-bore cameras view the subject in a treatment position in which most or all of the support surface is inside of the bore.

24. A method according to any of items 13-23, wherein one or more of the plurality of cameras is a time of flight camera.

25. A method according to item 24, comprising, for each time of flight camera, determining a spatial average of a plurality of pixels, each of the plurality of pixels corresponding to a respective distance measurement to a respective point on the surface of the subject.

What is claimed is:

1. A radiotherapy device comprising:

a rotatable gantry comprising a front, a rear and a bore, and a radiotherapy treatment device configured to deliver a therapeutic dose of radiation therapy to a subject positioned within the bore;

a support surface moveable into the bore from a side of the radiotherapy device corresponding to the front of the rotatable gantry;

a plurality of cameras for monitoring a subject that is located on the support surface, the plurality of cameras including a rear camera disposed outside of the bore and adjacent to the rear of the rotatable gantry, wherein the rear camera is a time of flight camera;

one or more near-bore cameras disposed on or adjacent to the front of the rotatable gantry or disposed on or adjacent to an interior of the bore proximal to the front of the rotatable gantry, wherein the rear camera and the one or more near-bore cameras have at least partially overlapping views and are arranged to view the subject in a treatment position in which most or all of the support surface is inside of the bore; and a controller configured to determine an average of distance measurements to a surface of the subject over a plurality of pixels of the rear camera, wherein the controller is further configured to use the determined average of distance measurements and location data from the one or more near-bore cameras to verify that the subject is positioned for accurate delivery of radiotherapy treatment to one or more target regions within the subject and to control the radiotherapy treatment device to deliver the therapeutic dose of radiation therapy to the subject positioned within the bore as verified.

2. The radiotherapy device according to claim 1, wherein the rear camera is disposed at a vertical height above a vertical height of the support surface, and/or wherein the rear camera is disposed at a vertical height above the vertical height of a central axis of the bore.

3. The radiotherapy device according to claim 1, wherein the one or more near-bore cameras are disposed at a vertical height above a vertical height of the support surface and below a vertical height of a top of the radiotherapy device.

4. The radiotherapy device according to claim 1, wherein the one or more near-bore cameras comprise a first near-bore camera disposed towards a left edge of the bore relative to a central axis of the bore, and a second near-bore camera disposed towards a right edge of the bore relative to the central axis of the bore.

5. The radiotherapy device according to claim 1, wherein the plurality of cameras comprise one or more setup cameras disposed outside the bore and located on a side of the radiotherapy device corresponding to the front of the rotatable gantry.

6. The radiotherapy device according to claim 5, wherein the one or more setup cameras are disposed at a vertical height above a vertical height of a top of the bore.

7. The radiotherapy device according to claim 5, wherein the one or more setup cameras comprise a first setup camera disposed left of the bore relative to a central axis of the bore, and a second setup camera disposed right of the bore relative to the central axis of the bore.

8. The radiotherapy device according to claim 5, wherein at least the one or more setup cameras are arranged to view the subject in a setup position in which most or all of the support surface is outside of the bore.

9. The radiotherapy device according to claim 1, wherein multiple of the plurality of cameras are time of flight cameras.

10. The radiotherapy device of claim 1, where the controller is configured to determine an average of distance measurements to the surface of the subject over a plurality of pixels of the one or more near-bore cameras, wherein the controller is further configured to use the determined average of distance measurements from both the rear camera and the one or more near-bore cameras to verify that the subject is positioned for accurate delivery of radiotherapy treatment to one or more target regions within the subject.

11. A method for imaging a subject using a radiotherapy device comprising a rotatable gantry including a radiotherapy treatment device configured to deliver a therapeutic dose of radiation therapy to a subject positioned within a bore, a support surface, a controller, and a plurality of cameras, the method comprising:

moving the support surface with the subject disposed thereon into the bore of the rotatable gantry from a side of the radiotherapy device corresponding to a front of the rotatable gantry;

obtaining one or more images of the subject using a rear camera of the plurality of cameras, the rear camera being disposed outside of the bore and adjacent to a rear of the rotatable gantry, wherein the rear camera is a time of flight camera;

obtaining one or more images of the subject using one or more near-bore cameras of the plurality of cameras, wherein the one or more near-bore cameras are disposed on or adjacent to the front of the rotatable gantry or disposed on or adjacent to an interior of the bore proximal to the front of the rotatable gantry, wherein the rear camera and the one or more near-bore cameras have at least partially overlapping views and are arranged to view the subject in a treatment position in which most or all of the support surface is inside of the bore;

determining, using the controller, an average of distance measurements to a surface of the subject over a plurality of pixels of the rear camera; and using the determined average of distance measurements and location data from the one or more near-bore cameras, verifying that the subject is positioned for accurate delivery of radiotherapy treatment to one or more target regions within the subject and controlling radiation treatment device to deliver the therapeutic dose of radiation therapy to the subject positioned within the bore as verified.

12. The method according to claim 11, further comprising:

with the subject disposed on the support surface and before moving the support surface into the bore, obtaining one or more further images of the subject using one or more cameras of the plurality of cameras.

13. The method according to claim 11, wherein the rear camera is disposed at a vertical height above a vertical height of the support surface, and/or wherein the rear camera is disposed at a vertical height above a vertical height of a central axis of the bore.

14. The method according to claim 11, wherein the one or more near-bore cameras are disposed at a vertical height above a vertical height of the support surface and below a vertical height of a top of the radiotherapy device, and wherein the one or more near-bore cameras comprise a first near-bore camera disposed towards a left edge of the bore relative to a central axis of the bore, and a second near-bore camera disposed towards a right edge of the bore relative to the central axis of the bore.

15. The method according to claim 14, wherein at least the rear camera and the one or more near-bore cameras view the subject in a treatment position in which most or all of the support surface is inside of the bore.

16. The method according to claim 11, wherein the plurality of cameras comprises one or more setup cameras disposed outside the bore and located on the side of the radiotherapy device corresponding to the front of the rotatable gantry, wherein the one or more setup cameras are disposed at a vertical height above a vertical height of a top of the bore, and wherein the one or more setup cameras comprise a first setup camera disposed left of the bore relative to a central axis of the bore, and a second setup camera disposed right of the bore relative to the central axis of the bore.

17. The method according to claim 16, wherein at least the one or more setup cameras view the subject in a setup position in which most or all of the support surface is outside of the bore.

18. The method according to claim 11, wherein multiple of the plurality of cameras are time of flight cameras.

19. The method of claim 11, further comprising determining an average of distance measurements to the surface of the subject over a plurality of pixels of the one or more near-bore cameras, and verifying that the subject is positioned for accurate delivery of radiotherapy treatment to one or more target regions within the subject further using the determined averages of distance measurements from both the rear camera and the one or more near-bore cameras.

\* \* \* \* \*